(12) United States Patent
Korkut

(10) Patent No.: US 9,068,160 B2
(45) Date of Patent: Jun. 30, 2015

(54) METHODS OF PRODUCING AN ANTISENSE VIRAL PARTICLE POPULATION

(76) Inventor: Asaf Korkut, Bethesda, MD (US)

( * ) Notice: Subject to any disclaimer, the term of this patent is extended or adjusted under 35 U.S.C. 154(b) by 611 days.

(21) Appl. No.: 12/863,351

(22) PCT Filed: Jan. 16, 2009

(86) PCT No.: PCT/US2009/031253
§ 371 (c)(1),
(2), (4) Date: Dec. 14, 2010

(87) PCT Pub. No.: WO2009/126348
PCT Pub. Date: Oct. 15, 2009

(65) Prior Publication Data
US 2011/0081318 A1    Apr. 7, 2011

Related U.S. Application Data

(60) Provisional application No. 61/021,706, filed on Jan. 17, 2008.

(51) Int. Cl.
*A61K 35/76*    (2015.01)
*C12N 7/01*    (2006.01)
*C12N 7/00*    (2006.01)

(52) U.S. Cl.
CPC ........ *C12N 7/00* (2013.01); *C12N 2740/16051* (2013.01); *C12N 2760/12151* (2013.01); *C12N 2760/14151* (2013.01); *C12N 2760/16151* (2013.01); *C12N 2760/20151* (2013.01); *C12N 2770/24151* (2013.01); *C12N 2770/24251* (2013.01)

(58) Field of Classification Search
None
See application file for complete search history.

(56) References Cited

PUBLICATIONS

Mariman et al, and Tellier et al, New strategies for AIDS theraphy and prohlylaxis, Nature vol. 318, 1985, p. 414.*
Kernodle et al, Expression of an Antisense hla Fragment in *Staphylococcus aureus* Reduces Alpha-Toxin Production In Vitro and Attenuates Lethal Activity in a Murine Model, Infectin and Immunity, 1997, vol. 65, pp. 179-184.*
Capodici et al., "Inhibition of HIV-1 Infection by Small Interfering RNA-Mediated RNA Interference," *The Journal of Immunology*, vol. 169, pp. 5196-5201, 2002.
Hanecak et al., "Antisense Oligonucleotide Inhibition of Hepatitis C Virus Gene Expression in Transformed Hepatocytes," *Journal of Virology*, vol. 71(8), pp. 5203-5212, 1996.
Lisziewicz et al., "Specific Inhibition of Human Immunodeficiency Virus Type 1 Replication by Antisense Oliguncleotides: An in vitro Model for Treatment," *Proc. Natl. Acad. Sci.*, vol. 89, pp. 11209-11213, 1992.
Mattion et al., "Reintroduction of Foot-and-Mouth Disease in Argentina: Characterisation of the Isolates and Development of Tools for the Control and Eradication of the Disease," *Vaccine*, vol. 22, pp. 4149-4162, 2004.

* cited by examiner

*Primary Examiner* — Maria Marvich
(74) *Attorney, Agent, or Firm* — Steven B. Kelber

(57) ABSTRACT

Methods for producing recombinant viruses, compositions including the viruses, and uses for the compositions are described herein.

5 Claims, No Drawings

METHODS OF PRODUCING AN ANTISENSE VIRAL PARTICLE POPULATION

CROSS REFERENCE TO RELATED APPLICATIONS

This application is a U.S. National Phase Application under 35 U.S.C. §371 of International Application PCT/US2009/031253, filed on Jan. 16, 2009, which claims priority to U.S. Provisional Application No. 61/021,706, filed on Jan. 17, 2008, the contents of which are incorporated herein by reference in their entireties.

TECHNICAL FIELD

This invention relates to viruses, and more particularly to recombinant viruses.

BACKGROUND

An antisense oligonucleotide is a single stranded nucleotide that hybridizes with a complementary nucleic acid (e.g., an mRNA) in a sequence-specific manner. The formation of a heteroduplex between the antisense oligonucleotide and mRNA interferes with expression of the mRNA in a cell. This interference is thought to occur by one or more of the following mechanisms: the heteroduplex triggers RNase H activity, leading to degradation of the complex; the heteroduplex prevents the RNAs from being translated into proteins by steric hindrance, or the heteroduplex interferes with mRNA maturation by inhibiting splicing and/or destabilizing mRNA. See, e.g., Chan et al., Clin. Exp. Pharm. Phys., 33:533-540, 2006.

SUMMARY

Provided herein are methods of producing recombinant viruses, nucleic acids encoding the viruses and portions thereof, and compositions including the viruses for use in modulating the function or effect of wild type viruses (i.e., non-recombinant viruses). More specifically, the recombinant viruses include a nucleotide fragment which is antisense to a portion of the wild type virus genome, e.g., a portion of the viral genome is deleted and replaced with a fragment which is the antisense sequence of the deleted region. The recombinant viruses are useful as antiviral agents, e.g., for inhibiting pathogenic effects of infection by natural, non-recombinant forms of the virus. Recombinant viruses are advantageous antiviral agents against the corresponding, natural viruses because they generally express the same capsid proteins, bind the same cellular receptors, and enter the same cell types as the natural viruses. Hence, they are targeted to the cells most susceptible to infection, where antiviral activities are desirable.

Accordingly, in one aspect, the invention features a method for producing a recombinant virus. The method includes, for example: providing a nucleic acid comprising a genome of a virus; contacting the nucleic acid with a nuclease under conditions in which the nuclease cleaves the nucleic acid, thereby producing fragments; determining the nucleotide sequence of one or more of the fragments; synthesizing oligonucleotides comprising a sequence antisense to of one or more of the fragments; ligating the nucleic acid fragments together in the presence of one or more of the antisense oligonucleotides (e.g., wherein the antisense oligonucleotide(s) are inserted such that they replace the region of the genome to which they are antisense, and wherein the fragments are ligated such that the fragments are connected in the order in which they are found in the original genome, but for the presence of the antisense fragment(s)) thereby producing a recombinant virus genome.

The method can further include: expressing the recombinant virus genome under conditions in which recombinant virus particles are produced; testing infectivity of the recombinant virus particles; selecting a population of virus particles that are infective; testing pathogenicity of the selected population; selecting a subpopulation of particles that reduce pathogenicity of infection when co-expressed in a cell with a wild type (e.g., non-recombinant) form of the virus.

In some embodiments, the method further includes testing the subpopulation of particles (or progeny thereof) for the ability to reduce pathogenicity or virulence of the wild type virus in vivo.

The method is applicable to any virus. For example, the virus is an animal virus, such as a virus infects mammals. In some embodiments, the virus is one which infects humans (e.g., wherein the virus is Hepatitis C virus, HIV, rabies virus, Ebola virus, a Hantavirus, West Nile Virus, or an influenza virus). Other viruses are described herein.

In some embodiments, the antisense oligonucleotides include sequences in which at least 20, 50, 100, or 250 nucleotides are antisense oligonucleotides.

The invention also features a virus produced by the methods described herein.

In another aspect, the invention features a method for producing a recombinant virus, which method includes: providing a nucleic acid comprising a genome of a virus; amplifying the genome (e.g., by PCR) in the presence of an oligonucleotide comprising a sequence antisense to a portion of the nucleic acid, thereby inserting an antisense sequence into the nucleic acid, wherein the sequence is antisense to a gene of the virus that is required for pathogenicity or virulence, and wherein expression of the antisense sequence inhibits expression of the gene; expressing the genome in a cell under conditions in which a virus is produced; thereby producing a recombinant virus.

The invention also features pharmaceutical compositions that include an antisense virus produced by a method described herein, and a pharmaceutically acceptable carrier.

In other aspects, the invention features a method for treating a viral infection in a subject by administering a composition including an antisense virus to the subject. The composition can be administered in an amount sufficient to inhibit a symptom of infection, or a symptom of virus-related disease, in the subject.

Antisense nucleic acids include oligonucleotides that specifically hybridize with one or more portions of the genome of the virus of interest. "Target nucleic acid" refers to the nucleotide sequence to which the antisense oligonucleotides hybridize. The mechanism believed to be operable when an antisense oligonucleotide modulates (e.g., decreases) expression of a target sequence is referred to herein as "antisense inhibition." Antisense inhibition is typically based upon hydrogen bonding-based hybridization of oligonucleotide strands or segments such that at least one strand or segment is cleaved, degraded, or otherwise rendered inoperable. Antisense oligonucleotides can interfere with processes that include DNA replication and transcription, translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

As used herein, "modulation" and "modulation of expression" mean either an increase (stimulation) or a decrease (inhibition) in the amount or levels of a nucleic acid molecule encoding a gene, e.g., DNA or RNA.

As used herein, "hybridization" means the pairing of complementary strands of oligomeric compounds. The preferred mechanism of pairing involves hydrogen bonding, which may be Watson-Crick, Hoogsteen or reversed Hoogsteen hydrogen bonding, between complementary nucleoside or nucleotide bases (also referred to herein as "nucleobases") of the strands of oligomeric compounds. For example, adenine and thymine are complementary nucleobases which pair through the formation of hydrogen bonds. Hybridization can occur under varying circumstances.

An antisense oligonucleotide is specifically hybridizable when binding of the compound to the target nucleic acid interferes with the normal function of the target nucleic acid to cause a change of activity (e.g., a loss of activity), and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). Preferably, antisense oligonucleotides comprise at least 70% sequence complementarity to a target region within the target nucleic acid, more preferably they comprise at least 90% sequence complementarity, and even more preferably comprise at least 95% sequence complementarity to the target region within the target nucleic acid sequence. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense oligonucleotide which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

As used herein, "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides may be preferred over native forms, for example, when modification provides for enhanced affinity for a target nucleic acid and/or increased stability in the presence of nucleases.

"Targeting" an antisense compound to a particular nucleic acid molecule, in the context of this invention, can be a multistep process. In some embodiments, the process begins with the identification of a target nucleic acid whose function is to be modulated. In other embodiments, the process involves generation of a population of antisense oligonucleotides and selection for those that exhibit a desired activity (e.g., inhibition of viral pathogenicity). This process is described herein. The target nucleic acid may be, for example, a cellular gene (or mRNA transcribed from the gene) whose expression is associated with a particular trait of the virus, e.g., virulence or pathogenicity, or a non-coding sequence (e.g., a regulatory sequence, such as an enhancer or promoter sequence).

The details of one or more embodiments of the invention are set forth in the description below. Other features, objects, and advantages of the invention will be apparent from the description and from the claims.

DETAILED DESCRIPTION

The inventions described herein relate to methods of producing recombinant viruses that include antisense sequence (also referred to as "antisense viruses"), compositions including the viruses, and their uses in treating and preventing viral infections. Antisense viruses are recombinant viruses that include in their genome a nucleotide sequence that is in antisense orientation relative to the sequence in a non-recombinant form of the virus. Antisense sequences bind to target sequences (e.g., coding sequences, non-coding sequences, mRNAs) of or expressed by the naturally occurring viruses. The formation of a heteroduplex between the antisense RNA and mRNA of the wild type virus interferes with expression of the mRNA, e.g., because the heteroduplex is susceptible to digestions by RNase H; the heteroduplex blocks translation of the mRNA in the complex; or the heteroduplex interferes with mRNA maturation by inhibiting splicing and/or destabilizing mRNA. See, e.g., Chan et al., *Clin. Exp. Pharm. Phys.,* 33:533-540, 2006. The antisense viruses described herein are infective and are selected for possessing a desirable biological characteristic (e.g., inhibition of pathogenicity and/or virulence when co-expressed with a wild type form of the virus), and thus provide a means for modulating viruses, e.g., for antiviral therapy or vaccination.

An antisense virus includes a viral coat necessary for infecting cells, a nucleic acid with an antisense fragment, e.g., a region which is antisense to a section of a target gene, such as a gene required for virulence. For example, the antisense fragment encodes antisense RNA that binds and inactivates mRNA encoded by the target sequence (e.g., target gene). Typically, the nucleic acid of the antisense virus genome is the same, or nearly the same (e.g., at least 90%, 95%, 97%, or 99% identical) as the nucleic acid of the corresponding wild type virus, with the exception of the antisense fragment. The antisense viruses described herein also include viruses with multiple antisense fragments (e.g., 2, 3, 4, 5, or 6 antisense fragments). In these viruses, the nucleic acid sequence of the genome is also the same, or nearly the same, as the corresponding wild type virus, with the exception of the antisense fragments. The antisense fragments will usually replace the section of the sequence to which they are complementary. The antisense fragment can be part or all of the target gene, placed in antisense orientation. The length of the antisense fragment must be sufficient to permit the antisense RNA transcribed from the antisense fragment to bind and inactivate the mRNA encoded by the target gene of the naturally occurring virus.

Antisense viruses can be produced for use in treating or preventing disease caused by a wide variety of viruses. The antisense viruses described herein are generally intact, infective and replication competent viruses. They have the same host cell specificity as a wild type (e.g., non-recombinant, naturally occurring) form of the virus and thus deliver the antisense sequences to where naturally infecting viruses reside. The antisense viruses are engineered or selected for having a desired biological activity, such as the ability to reduce pathogenesis or virulence by its natural counterpart, when expressed in the same cell. The insertion of antisense sequence inactivates a region and renders the virus encoded by the genome competent to inhibit a biological activity of a wild type virus. When an antisense virus enters a cell which has already been infected by natural virus(es), the antisense virus will replicate and the antisense transcript (antisense RNA) will bind the natural transcript and inhibit its synthesis.

Antisense viruses can be generated for any type of virus. In various embodiments, the antisense virus is an antisense virus of an animal virus (e.g., a virus that infects birds or mammals, e.g., a human virus). For example, an antisense virus is produced for one of the following types of viruses: a picornavirus (e.g., an enterovirus such as poliovirus, hepatitis A virus, coxsackievirus; a rhinovirus; an aphthovirus such as Foot-and-mouth disease virus); a calicivirus (e.g., Norwalk virus); a togavirus (e.g., rubella virus; an alphavirus such as an equine encephalitis virus); a flavivirus (e.g., West Nile virus, yellow fever virus, dengue virus, hepatitis C virus); a coronavirus; a rhabdovirus (e.g., rabies); a filovirus (e.g., Marburg virus, Ebola virus); a paramyxovirus (e.g., measles, respiratory syncytial viruses, parainfluenza virus, mumps virus); an orthomyxovirus (e.g., influenza virus, such as an avian influenza, or a human influenza); a bunyavirus (e.g., hantavirus); an arenavirus (e.g., Lassa virus, lymphocytic choriomeningitis virus, Machupo virus, Junin virus); a reovirus (e.g., a rotavirus); a retrovirus (e.g., human immunodeficiency virus (HIV), human T-lymphotropic virus); a hepadnavirus (e.g., hepatitis B virus (HBV)); a parvovirus; a papovavirus (e.g., a polyomavirus, a papilloma virus); an adenovirus; a herpesvirus (e.g., herpes simplex virus (types I and II), Epstein-Barr virus, human herpes virus-6 (HHV6), human herpes virus-7 (HHV7), cytomegalovirus, varicella-zoster virus (VZV)); a poxvirus (e.g., smallpox, vaccinia); non-A and non-B hepatitis virus.

Antisense viruses are particularly useful for treatment of infections by viruses for which treatment options are limited or unknown, e.g., for emerging viruses such as Ebola, which are incompletely characterized, or avian influenza strains which have become infective for non-avian species (e.g., avian influenza strains that infect mammals, such as swine and/or humans). Antisense viruses are also useful for treatment of viruses that are non-responsive to conventional treatment, such as drug-resistant HIV strains.

One example of a suitable target sequence for antisense inhibition of human papillomaviruses lies in the E1 mRNA translation start site (see Alam et al., *Anticancer Res.* 25:765-778, 2005).

Methods of Producing Antisense Viruses

Antisense viruses can be generated by producing a heterogeneous population of viruses with antisense fragments inserted at random and selecting clones that exhibit a desired biological activity, such as the ability to reduce pathogenicity or virulence when co-expressed with the wild type virus. To produce a heterogeneous population of viruses with antisense fragments randomly inserted, any art-known procedure can be used. In one exemplary method, a clone of the wild type virus genome is provided. Methods of cloning virus genome sequences are known (see, e.g., Molecular Genetics of Animal Viruses, *Fundamental Virology*, Fields and Knipe, eds., Chapter 7, pages 123-150, Raven Press Ltd., NY, 1991). The genome is digested with a nuclease, or multiple nucleases, to produce fragments. Next, antisense oligonucleotides corresponding to some or all of the fragments are produced. In some embodiments, the oligonucleotides contain a portion which is antisense to the original genome fragment, and a portion that corresponds to the sequence in the original fragment. In some embodiments, the oligonucleotides are primarily antisense sequence.

Virus genome fragments are re-ligated together in the presence of the antisense fragments. The re-ligation process is performed sequentially with virus genome fragments such that the reassembled virus genome is identical to the original genome, but with one (or two, or three, or more) segments replaced with an antisense fragment. To achieve proper reassembly of the virus genome, genome fragments are separated after the initial nuclease digestion. When the fragments are to be re-ligated, contiguous segments are ligated in a stepwise fashion, to allow reconnection of the segments in the same order in which they are present in the original virus. When performing the re-ligation reactions, one or more of the original fragments is omitted from the reactions, and replaced with an oligonucleotide containing sequence antisense to that particular genome fragment. Ligated clones are introduced into cells permissive for viral replication, viruses are expressed and tested for a desired biological activity. In this manner, one can produce an antisense virus. This approach does not require that one would have characterized the genomic region replaced with the antisense sequence, prior to producing an antisense virus. For example, one need not know the identity or function of a gene that is targeted by the antisense sequence prior to producing the antisense virus.

In other embodiments, a sequence (e.g., a gene sequence or a sequence within a non-coding region) is selected a priori and specifically targeted.

Generally, the target sequence(s) will not be a structural genes (e.g., a gene encoding a gene product necessary for the assembly of infectious virus particles).

The following description is an exemplary method for targeting a selected sequence for antisense inhibition.

Where the target sequence is a gene, typically the inversion covers as much of the coding sequence of the target gene as possible, including the initiation codon (ATG), so that the antisense RNA expressed by the antisense virus binds effectively to the natural viral mRNA. Inverting a large portion of the coding sequence also reduces the possibility that the antisense virus itself will also possess the trait that is desired to be diminished in wild type viruses, e.g., pathogenicity or virulence.

The inversion is between, and as close as possible to, two unique restriction enzyme sites to facilitate construction of antisense clones. The two unique restriction enzyme sites can be either naturally existing or recombinantly created.

An antisense virus proviral molecular clone is constructed from a functional proviral molecular clone of a naturally occurring virus by inverting ("turning antisense") a section (i.e., part or all) of one or more sequences. The inverted section of a selected sequence is referred to as the "antisense fragment" herein. Suitable candidate sequences for inversion are genes that are required for pathogenicity and/or virulence or genomic regions involved in regulating the expression of such genes. In some embodiments, genes required for infectivity are not suitable targets.

The sequence inversion can be accomplished by conventional recombinant technologies. One strategy has been developed to construct any antisense virus proviral molecular clone easily and precisely (see, e.g., U.S. Pat. No. 6,107,062). Briefly, recombinant polymerase chain reaction (r-PCR or PCR) technology is employed. PCR technology is known to those skilled in the art. See U.S. Pat. Nos. 4,683,195 and 4,983,728 hereby incorporated by reference. The strategy can include the following steps First, inserting DNA encoding a naturally occurring virus into a DNA cloning vector. Molecular cloning vectors such as plasmids (including phagemids), bacterial phage lambda and cosmids, are useful as cloning vectors.

Next, selecting a section of the viral DNA to be inverted (e.g., part or all of a gene that encodes a protein product required for the naturally occurring virus to be pathogenic). The selected section of the viral DNA is flanked by a unique restriction enzyme site A at its 5' end and by another unique restriction enzyme site B at its 3' end. The unique restriction enzyme sites A and B are either naturally existing or recombinantly created.

Next, carrying out a polymerase chain reaction, using the selected section of the viral DNA as the template, and two specially designed "antisense primers" that target the selected section (in practice, the whole vector containing the whole proviral genome is typically used as the template—there is no need to isolate the selected section in view of the primers used). Antisense Primer 1 comprises at its 3' half a portion of DNA complementary to the 5' end of the selected section of the viral DNA, and at its 5' half a portion of DNA containing the unique restriction enzyme site B. Antisense Primer 2 comprises at its 3' half a portion of DNA complementary to the 3' end of the selected section of the viral DNA, and at its 5' half a portion of DNA containing the unique restriction enzyme site A. The PCR amplification product (the "antisense fragment"), when aligned with the naturally occurring section of the viral DNA, is antisense to the latter between the two unique restriction enzyme sites A and B.

Next, digesting the vector containing the naturally occurring viral DNA with restriction enzymes A and B to release the selected section of DNA; digesting the PCR amplification product with restriction enzymes A and B to release the antisense fragment.

Then the the antisense section of DNA is ligated into the vector in place of the selected sense section of DNA; and antisense virus proviral molecular clones are isolated by standard procedures of transforming appropriate strains of cells such as E. coli followed by colony screening.

After the proviral clone is isolated, viruses are produced by expression of the clone, and the viruses are tested for the presence of a selected biological activity (e.g., reduction in pathogenicity when co-expressed with wild type virus).

Evaluating Biological Activities of Antisense Viruses

After an antisense virus (or heterogeneous population of antisense viruses) is produced, the virus is tested for its ability to modulate infection by a wild type form of the virus. Initial steps of characterizing the virus will typically be performed in vitro, using cells permissive for infection by the virus. Suitable assays include those in which a characteristic of virus infection (e.g., virus-induced cell pathogenicity, cellular transformation) are monitored after infection with a wild type form of the virus. For example, cell pathogenicity induced by a wild type form of the virus is compared to cell pathogenicity in samples infected with both the antisense virus and the wild type form. A reduction in pathogenicity in cells infected with both the antisense virus and the wild type form indicates that the antisense virus inhibits pathogenicity of the wild type form. One of skill in the art can select the appropriate cell types and indicia of virus infection to be monitored based the type of virus being assayed. The ability of an antisense virus to modulate (e.g., inhibit) expression of a gene product of the wild type virus can also be measured directly, e.g., by quantitating expression of viral gene or gene product targeted by the antisense virus. Antisense viruses that exhibit desired characteristics in vitro are further tested in suitable animal models to evaluate the ability to modulate infection in vivo.

Methods of Use

The recombinant viruses described herein have prophylactic and therapeutic uses, e.g., for veterinary and medical applications. The recombinant viruses can be incorporated into pharmaceutical compositions. The compositions include, for example, virus particles in a pharmaceutically-acceptable carrier, and/or combined with other medicinal agents, adjuvants, diluents, etc. Preferably, virus compositions will be administered so as to contact (e.g., infect) cells that are exposed to the corresponding wild type virus in the course of infection. Administration of the recombinant virus particles to a human subject or an animal in need thereof can be by any means known in the art for administering virus vectors.

Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or supenisions, solid forms suitable for solution or suspensions in liquid prior to injection, or as emulsions. Alternatively, one may administer a recombinant virus composition in a local rather than systemic manner, for example in a depot or sustained-release formation.

A "therapeutically-effective" amount as used herein is an amount of that is sufficient to alleviate (e.g., mitigate, decrease, reduce) at least one of the symptoms associated with a disease state. Alternatively stated, a "therapeutically-effective" amount is an amount that is sufficient to provide some improvement in the condition of the subject.

In embodiments particularly useful for viruses that infect mucosal surfaces, a recombinant virus composition is administered to the lungs of a subject by administering an aerosol suspension of respirable recombinant virus particles, which the subject inhales. The respirable particles may be liquid or solid. Aerosols of liquid particles may be produced by any suitable means, such as with a pressure-driven aerosol nebulizer or an ultrasonic nebulizer, as is known to those of skill in art. See, e.g. U.S. Pat. No. 4,501,729. Aerosols of solid particles comprising the recombinant virus composition may likewise be produced with any solid particulate medicament aerosol generator, by techniques known in the pharmaceutical art.

Dosages of the inventive virus particles will depend upon the mode of administration, the disease or condition to be treated, the individual subject's condition, and the particular virus vector, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$ transducing units or more, preferably about $10^8$-$10^{13}$ transducing units, yet more preferably $10^{12}$ transducing units.

In particular embodiments of the invention, more than one administration (e.g., two, three, four, or more administrations) may be employed to achieve therapeutic levels of gene expression.

A number of embodiments of the invention have been described. Nevertheless, it will be understood that various modifications may be made without departing from the spirit and scope of the invention. Accordingly, other embodiments are within the scope of the following claims.

What is claimed is:

1. A method for producing a recombinant antisense viral particle population, the method comprising:
   A) randomly fragmenting a parental viral genome to produce viral genome fragments,
   B) producing an anti-sense oligonucleotide corresponding to each of the different viral genome fragments,
   C) producing multiple recombinant viral genomes each comprising one of the different anti-sense oligonucleotides wherein each recombinant viral genome is produced by ligating the one antisense oligonucleotide to all of the viral genome fragments less the fragment corresponding to the one antisense oligonucleotide sequence, and
   D) transducing a host cell with each of the multiple recombinant viral genomes for expression of a recombinant viral particle from each of the multiple recombinant viral genomes thus producing a recombinant viral population comprising the multiple viral particles,
   E) testing the recombinant viral population to determine if the viral particles are infective
   F) determining if the infective recombinant viral particles have reduced pathogenicity as compared with that of viral particles encoded by said parental viral genome wherein the infective viral particles with reduced pathogenicity form the recombinant antisense viral population.

2. The method of claim 1, wherein said parental viral genome encodes a virus which is an animal virus.

3. The method of claim 2, wherein said virus infects mammals.

4. The method of claim 2, wherein said virus infects humans.

5. The method of claim 1, wherein each of said antisense oligonucleotides is no more than 250 nucleotide sequences in length.

* * * * *